(12) United States Patent
Reimer et al.

(10) Patent No.: US 11,464,635 B2
(45) Date of Patent: Oct. 11, 2022

(54) HEART VALVE WITH CHORDAL CAPTURE ELEMENTS FOR STABILIZATION

(71) Applicant: St. Jude Medical, Cardiology Division, Inc., St. Paul, MN (US)

(72) Inventors: Jay Reimer, Saint Paul, MN (US); Brandon Moore, Leesburg, VA (US); Chad Joshua Green, Forest Lake, MN (US); Paul E. Ashworth, Danbury, WI (US); Neelakantan Saikrishnan, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 392 days.

(21) Appl. No.: 16/567,214

(22) Filed: Sep. 11, 2019

(65) Prior Publication Data

US 2020/0085576 A1    Mar. 19, 2020

Related U.S. Application Data (60) Provisional application No. 62/730,612, filed on Sep. 13, 2018.

(51) Int. Cl.
*A61F 2/24* (2006.01)

(52) U.S. Cl.
CPC .......... *A61F 2/2454* (2013.01); *A61F 2/2418* (2013.01); *A61F 2220/0016* (2013.01)

(58) Field of Classification Search
CPC ..... A61F 2/2454; A61F 2/2457; A61F 2/2418
See application file for complete search history.

(56) References Cited

U.S. PATENT DOCUMENTS

| 10,179,042 B2 * | 1/2019 | Braido | A61F 2/2409 |
| 10,799,356 B2 * | 10/2020 | McAfee | A61F 2/2457 |
| 2009/0099410 A1 * | 4/2009 | De Marchena | A61B 17/00234 128/898 |

\* cited by examiner

*Primary Examiner* — Brian A Dukert
(74) *Attorney, Agent, or Firm* — Wei & Sleman LLP (57) ABSTRACT

An apparatus for stabilizing a prosthetic heart valve within an atrioventricular valve includes a collapsible and expandable stent having an inflow end, an outflow end, and struts forming a plurality of cells connected to one another in a plurality of annular rows around the stent. The stent further includes a collapsible and expandable valve assembly secured to the stent. The valve assembly includes a cuff and a plurality of leaflets having an open configuration and a closed configuration. A cord connected to the stent includes an attachment device adapted to couple the stent to heart tissue of a patient. A method of stabilizing a prosthetic heart valve within an atrioventricular valve annulus is also described.

4 Claims, 6 Drawing Sheets

*FIG. 1*

(PRIOR ART)

HEART VALVE WITH CHORDAL CAPTURE ELEMENTS FOR STABILIZATION

CROSS-REFERENCE TO RELATED APPLICATIONS

This application claims the benefit of the filing date of U.S. Provisional Patent Application No. 62/730,612 filed Sep. 13, 2018, the disclosure of which is hereby incorporated herein by reference.

BACKGROUND OF THE INVENTION

The present invention generally relates to valve repair and, more particularly, to apparatus and methods for stabilizing a prosthetic heart valve.

Properly functioning heart valves maintain unidirectional blood flow in the circulatory system by opening and closing, depending on the difference in the pressure on opposite sides of the valve. The two atrioventricular valves (mitral and tricuspid valves) are multicusped valves that prevent backflow from the ventricles into the atria during systole.

The mitral valve is located at the gate of the left ventricle and is made up of two leaflets and a diaphanous incomplete ring around the valve, known as the mitral valve annulus. When the valve opens, blood flows from the left atrium into the left ventricle. After the left ventricle fills with blood and contracts, the two leaflets of the mitral valve are pushed upwards and close, preventing blood from flowing back into the left atrium and the lungs.

Mitral valve disease may cause at least one of the mitral valve leaflets to prolapse, preventing the leaflets from properly coapting. In some instances, mitral valve disease may also cause dilation of the valve annulus and/or the left ventricle. As a result, when the ventricle contracts, blood is allowed to return to the left atrium and the lungs. This phenomenon is known as mitral regurgitation.

Untreated mitral regurgitation may lead to congestive heart failure and pulmonary hypertension. For this reason, mitral regurgitation is often treated by replacing the entire mitral valve either through a surgical or transcatheter procedure, banding the outer surface of the left ventricle to modify the shape of the ventricular wall, repairing the mitral valve leaflets, and other interventional procedures.

Diseased mitral valves, however, typically lack calcification on the native annulus and/or leaflets, and in turn rigidity, complicating the stabilization of prosthetic mitral valves within the native annulus. As a result, prosthetic mitral valves are highly susceptible to migrating from the desired position. The risk of prosthetic mitral valve migration is further increased when mitral valve disease has caused the left ventricle and/or the native valve annulus to dilate.

Despite the improvements that have been made to these procedures, various shortcomings remain. For example, these procedures either entail invasive open heart surgery, with its attendant risks and extended recovery period; or in the case of transcatheter valve replacement, may require supplemental stabilization, apart from the radial force exerted by the valve stent on the native valve annulus.

There therefore is a need for improvements to the devices and methods for stabilizing prosthetic atrioventricular valves, thereby allowing the prosthetic heart valve to be inserted and deployed using minimally invasive techniques.

BRIEF SUMMARY OF THE INVENTION

In accordance with a first aspect of the present invention, a device for stabilizing a prosthetic heart valve within a diseased atrioventricular valve is provided. Among other advantages, the device allows the diseased valve to be repaired using minimally invasive techniques.

One embodiment of the apparatus includes a collapsible and expandable stent with an inflow end and an outflow end and a collapsible and expandable valve assembly including a cuff and a plurality of leaflets having an open configuration and a closed configuration. The stent further includes struts forming a plurality of cells connected to one another in a plurality of annular rows around the stent and a cord connected to the stent. The cord includes an attachment device adapted to couple the stent to heart tissue of a patient.

A method of reducing ventricular dilation includes attaching a first end of a cord to a first papillary muscle, attaching a second end of the cord to a second papillary muscle different than the first papillary muscle, applying a clamp to an portion of the cord between the first end and the second end, tensioning the cord between the first and second papillary muscles, and moving at least one of the first papillary muscles and the second papillary muscle toward one another. Reducing ventricular dilation may, in some cases, restore proper valve function. In other instances, valve repair may be desired.

A method of stabilizing a prosthetic valve within an atrioventricular valve includes delivering a collapsible and expandable stent including a collapsible and expandable valve assembly and a first cord provided with an attachment device to a location proximate the valve annulus and coupling the attachment device to at least one of the inner ventricular wall and a papillary muscle of a patient.

BRIEF DESCRIPTION OF THE DRAWINGS

Various embodiments of the present disclosure are described herein with reference to the following drawings in which.

DETAILED DESCRIPTION

Figure 1:
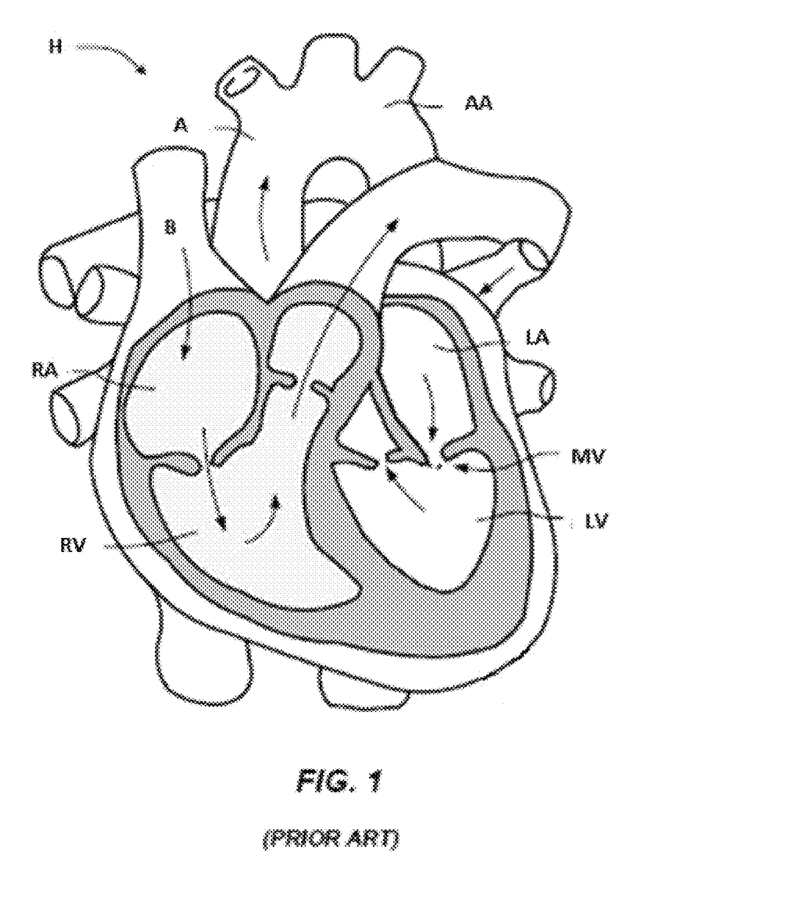
FIG. 1 is a schematic cutaway view of a human heart.

FIG. 1 is a schematic representation of a human heart H. The human heart includes two atria and two ventricles: a right atrium RA and a left atrium LA, and a right ventricle RV and a left ventricle LV. Blood flows through the heart H in the direction shown by arrows "B". As illustrated in FIG. 1, the heart H further includes an aorta A and an aortic arch AA. Disposed between the left atrium LA and the left ventricle LV is the mitral valve MV. The mitral valve MV, also known as the bicuspid valve or left atrioventricular valve, is a bi-leaflet valve that opens as a result of increased pressure in the left atrium, relative to the left ventricle, as the left atrium fills with blood.

Figures 2A, 2B:
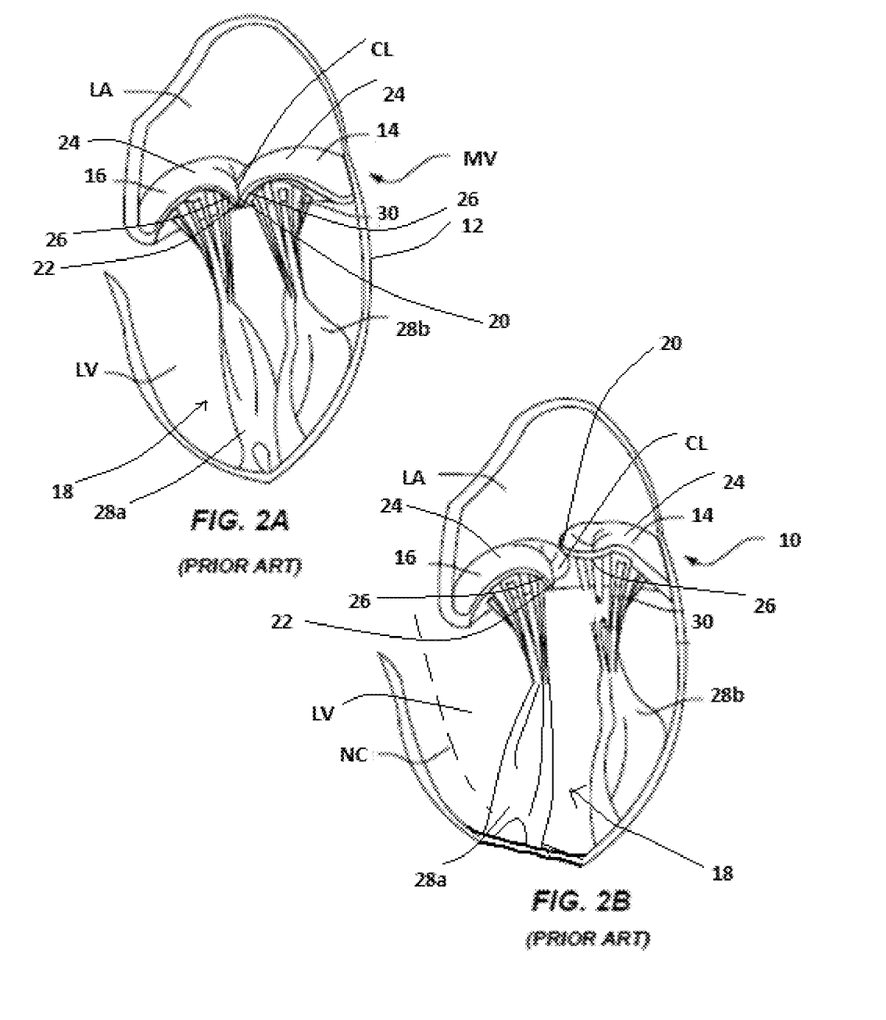
FIG. 2A is a schematic representation of a native mitral valve and associated structures during normal operation.
FIG. 2B is a schematic representation of a diseased mitral valve and associated structures having a prolapsed leaflet and a dilated left ventricle.

A typical mitral valve MV, an example of which is shown in FIG. 2A, includes an annulus 12, a posterior leaflet 14, an anterior leaflet 16, and sub-valvular structure 18. Annulus 12 is a dense ring of fibrous tissue which lies at the juncture between the left atrium and the left ventricle. Posterior leaflet 14 and anterior leaflet 16 are attached to annulus 12 and extend toward the valve orifice. The portions of posterior and anterior leaflets 14, 16 that extend toward the valve orifice are known as free edges 20, 22.

Posterior and anterior leaflets 14, 16 each have an upper portion 24 that, when the leaflets are closed, extends from annulus 12 to coaptation line CL in a direction that is generally perpendicular to the direction of blood flow through the valve, and a lower portion 26 that, when the leaflets are closed, extends downward from the coaptation line to the free edge of the leaflet in a direction that is generally parallel to the direction of blood flow through the valve. Posterior leaflet 14 and anterior leaflet 16 each have three scalloped portions.

Sub-valvular structure 18 includes two muscular projections that protrude from an inner wall of the left ventricle LV, known as papillary muscles 28a, 28b, and numerous chordae tendineae 30, thin fibrous bundles that emanate from the papillary muscles and that are attached to an outflow surface of the valve leaflets near the free edges 20, 22 of the scalloped portions or nearer the leaflet root.

During atrial systole, blood flows down the pressure gradient from the left atrium LA to the left ventricle LV. When the left ventricle LV contracts during ventricular systole, the increased blood pressure in the left ventricle LV pushes the mitral valve MV closed, preventing the backflow of blood into the left atrium LA. Since the blood pressure in left atrium LA is much lower than the blood pressure in left ventricle LV, posterior and anterior leaflets 14, 16 attempt to evert to the low pressure regions. Chordae tendineae 30 prevent the eversion by becoming tense, thus pulling posterior leaflet 14 and anterior leaflet 16 and holding them in the closed position.

FIG. 2B is a schematic representation of a diseased mitral valve 10 during ventricular systole. The ventricular wall has dilated with respect to its normal configuration illustrated in a dashed line and labelled "NC", and posterior leaflet 14 has prolapsed into the left atrium LA. Moreover, certain chordae tendineae 30 have stretched and others have ruptured. As a result, sub-valvular structure 18 can no longer adequately support and position posterior leaflet 14. Thus, diseased mitral valve 10 is incapable of functioning properly to prevent blood from returning to the left atrium and the lungs. For illustrative purposes, anterior leaflet 16 is depicted in a properly closed position (i.e., adjacent coaptation line CL), although it is recognized that any of the chordae tendineae 30 could stretch and/or rupture, causing either or both of posterior leaflet 14 and anterior leaflet 16 to prolapse.

The devices and methods described herein are adapted to stabilize a prosthetic heart valve in the native annulus to facilitate repair of the prolapsed leaflets of the valve. While the devices and methods are described herein in connection with the repair of the mitral valve, it will be appreciated that these concepts may be equally applicable to the repair of the tricuspid valve.

The prosthetic heart valve and stabilization features described hereinafter may be delivered to the desired site (i.e., adjacent mitral valve annulus 12) in a collapsed condition using any suitable delivery device. The delivery device may be introduced into the patient using a transfermoral, transapical, transseptal or any other percutaneous approach.

Figure 3:
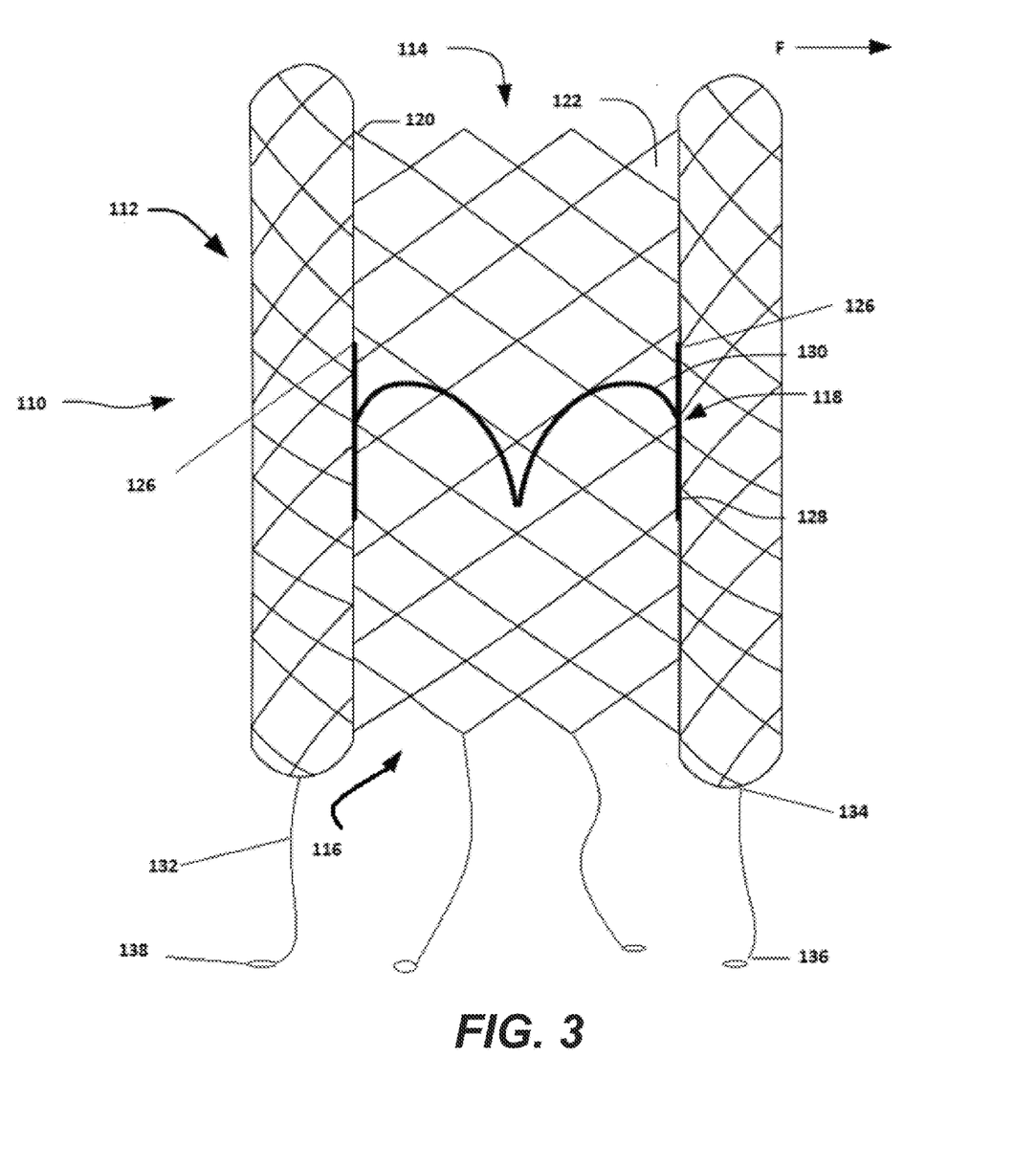
FIG. 3 is a schematic longitudinal cross-section of a prosthetic heart valve and stabilization features in accordance with an embodiment of the invention.

Prosthetic heart valve 110, shown in FIG. 3, includes a collapsible and expandable stent 112 having an inflow end 114 and an outflow end 116, and a valve assembly 118 secured to the stent. Stent 112 may be formed from biocompatible materials that are capable of self-expansion, for example, shape memory alloys such as nitinol. In its expanded configuration, stent 112 may be substantially cylindrical in shape and adapted to provide a radial force F against native mitral valve annulus 12 to assist in stabilizing prosthetic heart valve 110 within the annulus.

Stent 112 includes a plurality of struts 120 that form cells 122 connected to one another in one or more annular rows around the stent. Cells 122 may be substantially the same size both around the perimeter of stent 112 and along the length of the stent.

One or more retaining elements (not shown) may be provided on either the inflow end 114 or the outflow end 116 of stent 112 and sized and shaped to cooperate with a delivery device. Engagement of the retaining elements with a corresponding retaining structure in the delivery device maintains the position of prosthetic heart valve 110 within the delivery device, minimizes longitudinal movement of the prosthetic heart valve relative to the delivery device during unsheathing or resheathing procedures, and prevents rotation of the prosthetic heart valve relative to the delivery device as the delivery device is advanced to the target location and during deployment.

Stent 112 further includes a plurality of commissure features 126 for attaching the commissures between adjacent prosthetic heart valve leaflets to the stent. Commissure features 126 may include one or more eyelets which facilitate the suturing of the leaflet commissure to stent 112.

Valve assembly 118 may be secured to stent 112 by suturing the valve assembly to struts 120 and/or to commissure features 126. Valve assembly 118 includes a cuff 128 and a plurality of leaflets 130 which open and close collectively to function as a one-way valve. Because FIG. 3 illustrates a prosthetic heart valve 110 for replacing the native mitral valve, the prosthetic heart valve is illustrated with two leaflets 130. However, it will be understood that the prosthetic heart valve according to this aspect of the invention may include any number of leaflets and commissure features other than two, including three leaflets and three commissure features for tricuspid heart valve repair.

Although cuff 128 is illustrated in FIG. 3 as being disposed on the luminal or inner surface of stent 112, it is contemplated that the cuff may be disposed on the abluminal or outer surface of the stent, or may cover all or part of either or both of the luminal and abluminal surfaces. Both cuff 128 and leaflets 130 may be wholly or partly formed of any suitable biological material, such as bovine or porcine pericardium, or polymers, such as PTFE, urethanes and the like.

A plurality of cords 132 may be disposed circumferentially about stent 112. More particularly, each cord 132 may have a first end 134 secured at, or near, the outflow end 116 of stent 112 and a second or free end 136. Second ends 136 may include an attachment device 138 adapted to couple the stent to heart tissue, for example, to the inner ventricular wall and/or to one or more papillary muscles 28a, 28b as described in the various embodiments below.

Figure 4:
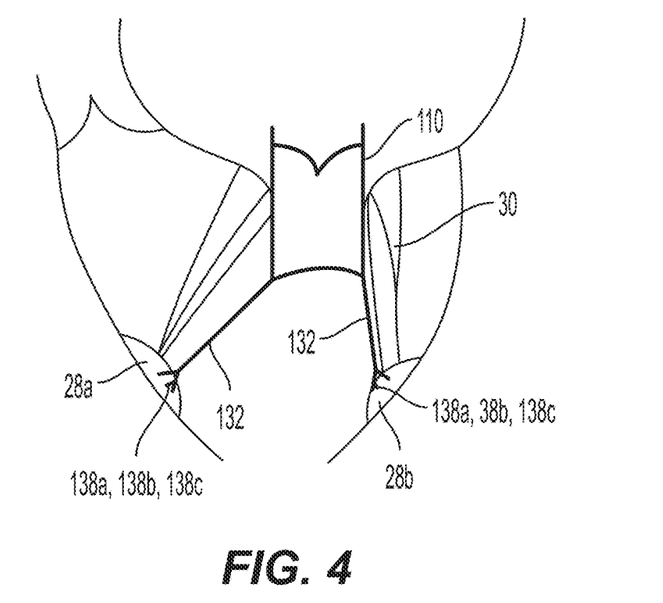
FIG. 4 is a schematic representation of the prosthetic heart valve of FIG. 3 coupled to a patient's papillary muscles.

The attachment device 138, as shown in FIG. 4, may be a mechanically compressive clasp for gripping the papillary muscles 28a, 28b. In a first embodiment, clasp 138a may include a pair of jaws formed from a plastically deformable material. Once a papillary muscle 28a, 28b is positioned between the jaws, the user may apply a compressive force to plastically deform the jaws toward one another, securing clasp 138a to the papillary muscle.

In an alternative embodiment, clasp 138b may include a spring that biases jaws of the clasp to a closed configuration, much like an alligator clip. To attach such clasp 138b to papillary muscle 28a, 28b, the user may apply a force sufficient to overcome the biasing force, thereby transitioning the jaws of the clasp to an open configuration. Once properly positioned around papillary muscle 28a, 28b, the force may be released to allow the jaws of clasp 138b to return to their closed configuration, thereby securing the clasp to the papillary muscle.

In yet another embodiment, clasps 138c may be formed of nitinol or another shape-memory material adapted to change shape to a configuration capable of grasping papillary muscle 28a, 28b upon exiting the lumen of a delivery device. To attach clasp 138c to papillary muscle 28a, 28b, the user may employ the delivery device to deliver prosthetic heart valve 110 to the target site and, in turn, the clasps to a desired location adjacent the papillary muscles. The user may then deploy clasps 138c from the lumen of the delivery device, whereupon the clasps will change shape and engage papillary muscles 28a, 28b. For example, clasps 138c may include a pair of jaws that are initially in an open configuration, as with clasps 138a, but which change shape to a closed configuration to capture the papillary muscles without the application of an external force.

While attachment device 138 is described above as a clasp 138a, 138b, 138c, it will be recognized that the attachment device may be any device adapted to couple cords 132 to papillary muscles 28a, 28b, for example, barbs, coils, or similar devices.

Once the second end 136 of each cord 132 is securely attached to at least one of papillary muscles 28a, 28b, the cords anchor stent 112 to the papillary muscles, providing a supplemental anchoring force that ensures that prosthetic heart valve 110 does not migrate toward the left atrium LA in the event that radial force F alone is insufficient to secure the prosthetic heart valve within native mitral valve annulus 12.

Figure 5:
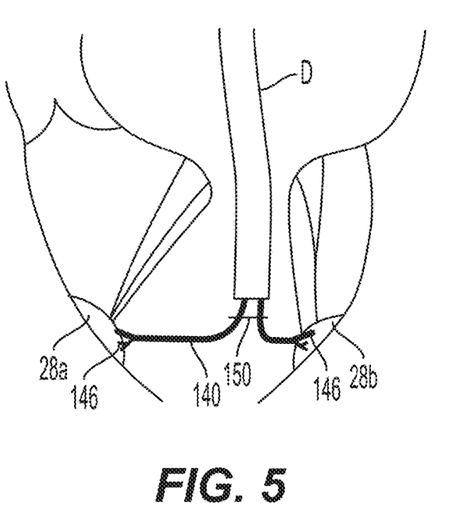
FIGS. 5-7 are schematic representations illustrating the use of a bridge to couple the prosthetic valve of FIG. 3 to a patient's papillary muscle.
Figure 6:
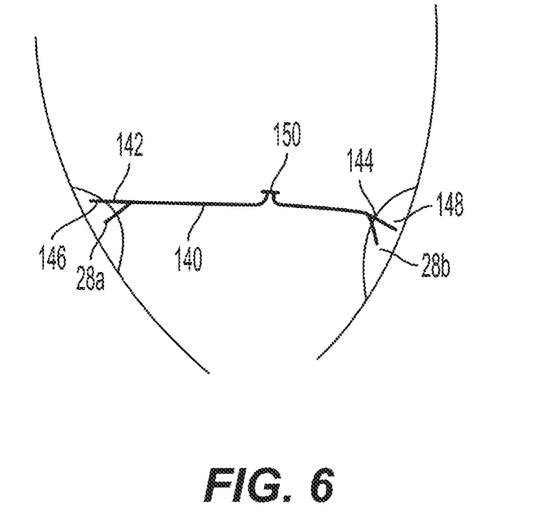
Figure 7:
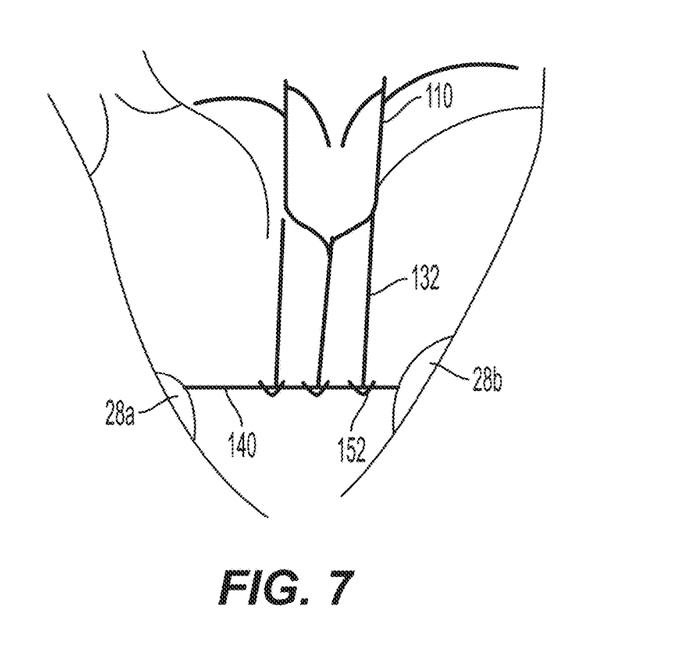

In another embodiment, illustrated by FIGS. 5-7, cords 132 may be indirectly and operatively coupled to papillary muscles 28a, 28b via a bridge 140. Prior to deploying prosthetic heart valve 110 in native mitral valve annulus 12, bridge 140 is attached and tensioned between papillary muscles 28a, 28b.

Bridge 140 may be a cable-like member having a first end 142 provided with a first clasp 146 and a second end 144 provided with a second clasp 148. Clasps 146 and 148 may be similar to any of the embodiments of clasps 138a, 138b, 138c described above. Bridge 140 may be a single continuous cable or may be formed from two or more cables that are connected together prior to or during securement of the bridge between papillary muscles 28a, 28b.

FIGS. 5 and 6 illustrate the coupling of bridge 140 between papillary muscles 28a, 28b. As shown in FIG. 5, bridge 140 may be delivered into the left ventricle LV via a delivery device D. Once positioned in the left ventricle, first clasp 146 may be deployed from the lumen of delivery device D and secured to papillary muscle 28a. Likewise, second clasp 148 may be deployed from the lumen of delivery device D and secured to papillary muscle 28b. First clasp 146 may be secured to papillary muscle 28a prior to, simultaneously with, or after second clasp 148 is secured to papillary muscle 28b.

After the clasps 146, 148 of bridge 140 have been attached to papillary muscles 28a, 28b, a clamp 150 may be applied to an intermediate portion of the bridge between the first end 142 and the second end 144, as shown in FIG. 5, to tension the bridge between the papillary muscles. As will be appreciated, the user may adjust the tension of bridge 140 by manipulating the position of clamp 150 on the bridge. The user may, for example, apply additional tension to bridge 140 by sliding clamp 150 closer to ends 142 and 144 of the bridge. Alternatively, the user may release tension by sliding or otherwise moving clamp 150 farther from ends 142 and 144 of the bridge.

When bridge 140 has been tensioned to overcome the natural forces applied by the ventricular wall, papillary muscles 28a, 28b will move toward one another, in turn moving the ventricular wall to which they are attached. Thus, by adjusting the position of clamp 150 on bridge 140, the user may be able to modify the shape of the left ventricle LV and, in some instances, return the left ventricle to its original shape. After the user has tensioned bridge 140 as desired, the user may apply a compressive force to clamp 150, securing the clamp to the bridge such that the clamp cannot be slid or otherwise be repositioned to further modify the tension of the bridge. As a result, an intermediate portion of bridge 140 may form a loop adjacent the bridge, as shown in FIG. 6. This loop may optionally be removed, for example, via a cutting edge provided on the clamp 150 configured to cut the bridge when the clamp is compressed thereto, or a separate cutting device.

In situations in which chordae tendineae 30 have not been stretched or ruptured, restoring the left ventricle LV to its original shape, or close to its original shape, may be sufficient to restore proper mitral valve function, rendering mitral valve replacement unnecessary.

With bridge 140 attached to and tensioned between papillary muscles 28a, 28b, prosthetic valve 110 may be coupled to the bridge, as shown in FIG. 7, by securing the attachment device 138 of one or more cords 132 to the bridge. Attachment device 138 may be any one of clasps 138a, 138b, 138c, as described above, for connecting to bridge 140, or alternatively, a hook 152 for looping underneath and engaging the bridge, thereby operatively coupling prosthetic valve 110 to the bridge.

Figure 8A:
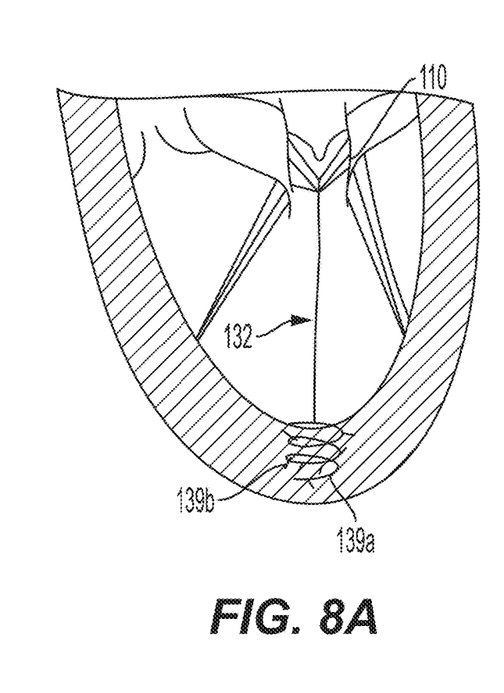
FIGS. 8A and 8B are schematic representations of the prosthetic heart valve of FIG. 3 coupled to a patient's inner ventricular wall.
Figure 8B:
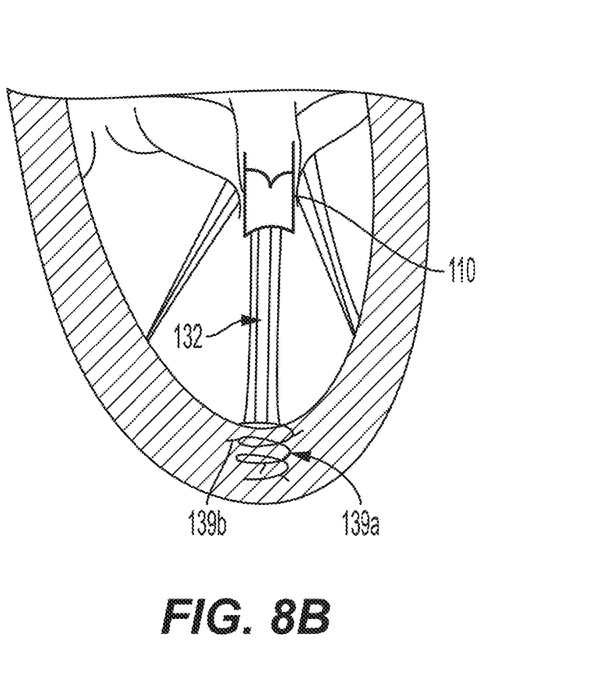

In another embodiment, shown in FIGS. 8A and 8B, attachment device 138 may be a coil 139a having a corkscrew-like configuration with a sharpened tip adapted to pierce the inner wall of the left ventricle, for example at the ventricular floor. Prosthetic heart valve 110 may include a single cord 132 with a coil 139a at its second end 136, as shown in FIG. 8A. Alternatively, prosthetic heart valve 110 may include a plurality of cords 132 with a single coil 139a at the second ends thereof, as shown in FIG. 8B. While only a single coil 139a is shown in FIGS. 8A and 8B, it will be appreciated that prosthetic valve 110 may be anchored to the ventricle wall by a plurality of such coils, each of which may be connected to the prosthetic heart valve by one or more cords 132.

To attach coil 139a to the inner ventricular wall, the user may use a delivery device to deliver prosthetic heart valve 110 to the target site. Once the delivery device has been properly positioned, the user may deploy attachment device 138 from the lumen of the delivery device and pierce the heart tissue at the ventricular floor with the tip of coil 139a. Coil 139a may then be turned to advance into the heart tissue, anchoring prosthetic heart valve 110 so that it does not migrate toward the left atrium.

Alternatively or additionally, attachment device 138 may include barbs 139b for engaging the inner ventricular wall. As with coils 139a, each barb 139b may be connected to the second end 136 of a single cord 132 or to the second ends of a plurality of cords. To attach barbs 139b to the inner ventricular wall, the user may deliver prosthetic heart valve 110 to the target site via a delivery device. After the delivery device has been properly positioned, the user may deploy attachment device 138 from the lumen of the delivery device and press the barbs 139b to penetrate the inner ventricular wall. It will be appreciated that prosthetic heart valve 110 may be anchored to the ventricular wall by one or a plurality of barbs 139b, each connected to the prosthetic heart valve by one or more cords 132.

Whether attachment device 138 is a coil 139a or a barb 139b, the attachment device may include a roughened or sticky surface to improve engagement with the ventricular wall. Moreover, attachment device 138 may be semi-permeable and/or include bioactive molecules to promote tissue ingrowth of the ventricular wall.

Figure 9:
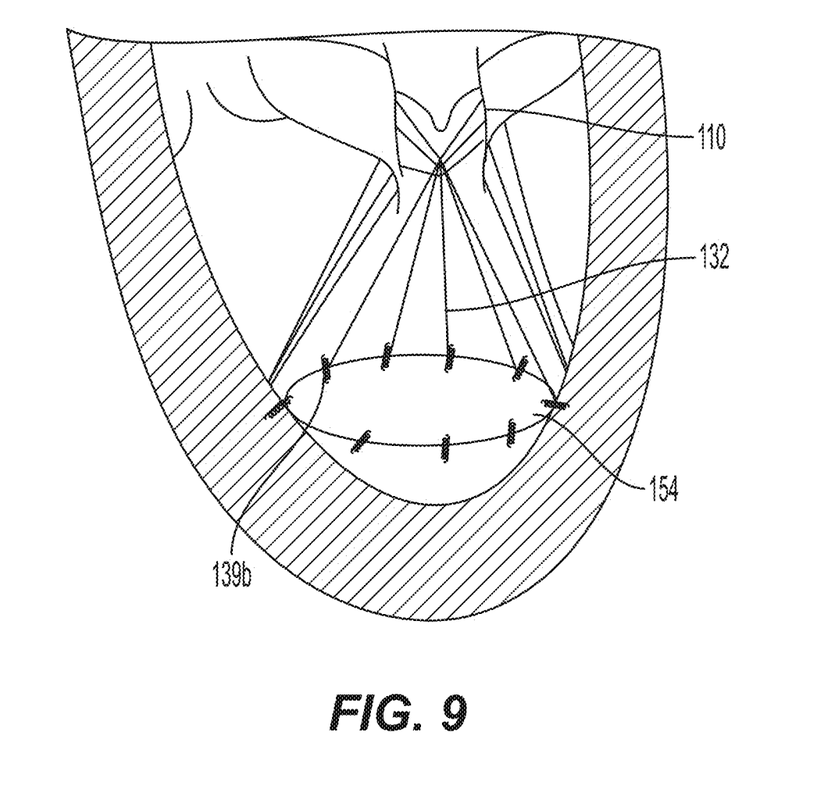
FIG. 9 is a schematic representation illustrating the use of a ring to couple the prosthetic heart valve of FIG. 3 to a patient's inner ventricular wall.

FIG. 9 illustrates an embodiment in which cords 132 are indirectly and operatively coupled to the ventricular wall via a ring 154. Ring 154 may be formed from biocompatible materials that are capable of self-expansion, for example, shape memory alloys such as nitinol. An underside of ring 154 may include coils, such as coils 139a and/or barbs, such as barbs 139b, for attaching the ring to the inner ventricular wall at, or near, the ventricular floor.

Ring 154 may be loaded within a delivery device in a collapsed configuration and delivered to the desired site within left ventricle LV. Once the delivery device has been properly positioned, the user may deploy ring 154, allowing the ring to transition to an expanded configuration as shown in FIG. 9. Coils 139a and/or barbs 139b may then be implanted individually within the inner ventricular wall.

After ring 154 has been securely connected to the heart tissue, prosthetic heart valve 110 may be attached to the ring in the same manner as the prosthetic heart valve was attached to bridge 140. Specifically, clasps 138a, 138b, 138c, or hooks 152 provided on the second ends 136 of one or more cords 132 may be attached around the perimeter of anchoring ring 154, thus advantageously distributing the anchoring forces around a perimeter of the inner ventricular wall.

In any of the above described embodiments, prosthetic heart valve 110 is anchored to heart tissue, for example, to at least one papillary muscle and/or to the inner ventricular wall, thereby providing stabilization forces that are supplemental to the radial force applied by the heart valve stent. The anchoring structures described above enable the diseased mitral valve to be repaired using only minimally invasive techniques and promote the prolonged function of the prosthetic valve by ensuring that the prosthetic heart valve does not migrate from its desired position.

To summarize the foregoing, one aspect of the present disclosure is directed to a prosthetic heart valve including a collapsible and expandable stent having an inflow end and an outflow end, the stent including struts forming a plurality of cells, the plurality of cells being connected to one another in a plurality of annular rows around the stent; a collapsible and expandable valve assembly secured to the stent, the valve assembly including a cuff and a plurality of leaflets having an open configuration and a closed configuration; a cord connected to the stent; and an attachment device operatively connected to the cord and configured to couple the stent to heart tissue of a patient; and/or wherein the attachment device is selected from the group consisting of coils barbs or combinations thereof adapted to engage the heart valve of the patient; and/or further comprising a collapsible and expandable ring having a plurality of the attachment devices spaced around the ring and adapted to engage the heart tissue of the patient; and/or wherein the attachment devices are selected from the group consisting of coils, barbs or combinations thereof; and/or further comprising an attachment member connected to the cord and operative to couple the cord to the ring, the attachment member being selected from the group consisting of clasps, hooks or a combination thereof; and/or further comprising a plurality of cords connected to the stent, each of the cords including one of the attachment members operative to couple the cord to the ring; and/or wherein the attachment device is selected from the group consisting of clasps, barbs, coils or combinations thereof configured to couple the stent to the papillary muscles of the patient; and/or further comprising a bridge adapted to be coupled between a first papillary muscle and a second papillary muscle of the patient; and/or further comprising a clamp for tensioning the bridge; and/or wherein the bridge includes a first clasp configured to attach to the first papillary muscle and a second clasp configured to attach to the second papillary muscle; and/or further comprising an attachment member connected to the cord and operative to couple the cord to the bridge, the attachment member being selected from the group consisting of clasps, hooks or combinations thereof.

Another aspect of the present disclosure is directed to a method of stabilizing a prosthetic heart valve, the method comprising: delivering a prosthetic heart valve to a location proximate an atrioventricular valve annulus in a patient, the prosthetic heart valve including a collapsible and expandable stent, a collapsible and expandable valve assembly secured to the stent, a cord connected to the stent, and an attachment device; expanding the prosthetic heart valve in the atrioventricular annulus; and coupling the attachment device to heart tissue of a patient; and/or wherein the attachment device is a clasp and the clasp is attached directly to a papillary muscle of the patient; and/or wherein the attachment device is a coil or a barb that is connected directly to the inner ventricular wall of the patient; and/or further comprising implanting a ring into the inner ventricular wall of the patient; and/or further comprising coupling the cord to the ring; and/or further comprising: attaching a bridge to a first papillary muscle and to a second papillary muscle different than the first papillary muscle; applying a clamp to the bridge between the first papillary muscle and the second papillary muscle; and sliding the clamp along the bridge to tension the bridge; and/or further comprising sliding the clamp along the bridge to move the first papillary muscle relative to the second papillary muscle to modify the shape of the ventricular wall of the patient; and/or further comprising operatively connecting the cord to the bridge.

In yet another aspect of the present disclosure, a method of reducing ventricular dilation comprises: operatively attaching a first end of a cord to a first papillary muscle; operatively attaching a second end of the cord to a second papillary muscle different than the first papillary muscle; applying a clamp to the cord between the first end and the second end; and sliding the clamp along the cord to adjust a position of the first papillary muscle relative to the second papillary muscle.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
   a collapsible and expandable stent having an inflow end and an outflow end, the stent including struts forming a plurality of cells, the plurality of cells being connected to one another in a plurality of annular rows around the stent;
   a collapsible and expandable valve assembly secured to the stent, the valve assembly including a cuff and a plurality of leaflets having an open configuration and a closed configuration;
   a cord connected to the stent;
   an attachment device operatively connected to the cord;
   a bridge adapted to be coupled between a first papillary muscle and a second papillary muscle of the heart; and
   a sliding clamp coupled to the bridge configured to adjust tension of the bridge;
   wherein the cord is connected to the bridge via the attachment device.

2. The apparatus of claim 1, wherein the attachment device is selected from the group consisting of clasps, barbs, coils or combinations thereof configured to couple the stent to the papillary muscles of the patient.

3. The apparatus of claim 1, wherein the sliding clamp is configured to modify a shape of a left ventricle of the heart.

4. The apparatus of claim 1, wherein the bridge includes a first clasp configured to attach to the first papillary muscle and a second clasp configured to attach to the second papillary muscle.

* * * * *